(12) United States Patent
O'Connor

(10) Patent No.: US 8,754,269 B2
(45) Date of Patent: Jun. 17, 2014

(54) CATALYTIC PROCESS FOR REACTING CARBON DIOXIDE WITH HYDROGEN

(75) Inventor: Paul O'Connor, Hoevelaken (NL)

(73) Assignee: Antecy B.V., Hoevelaken (NL)

( * ) Notice: Subject to any disclaimer, the term of this patent is extended or adjusted under 35 U.S.C. 154(b) by 50 days.

(21) Appl. No.: 13/490,486

(22) Filed: Jun. 7, 2012

(65) Prior Publication Data

US 2013/0005839 A1 Jan. 3, 2013

Related U.S. Application Data

(63) Continuation of application No. PCT/EP2010/069305, filed on Dec. 9, 2010.

(60) Provisional application No. 61/285,227, filed on Dec. 10, 2009.

(51) Int. Cl.
  *C07C 29/149* (2006.01)
(52) U.S. Cl.
  USPC .......................................................... 568/885
(58) Field of Classification Search
  USPC .......................................................... 568/885
  See application file for complete search history.

(56) References Cited

U.S. PATENT DOCUMENTS

| 4,339,547 A | 7/1982 | Corbett et al. |
| 2005/0232833 A1 | 10/2005 | Hardy et al. |
| 2007/0149392 A1 | 6/2007 | Ku et al. |

FOREIGN PATENT DOCUMENTS

| DE | 10156975 A1 | 6/2003 |
| DE | 20320020 U1 | 6/2004 |
| GB | 2418430 A | 3/2006 |
| GB | 2459430 A | 10/2009 |
| WO | WO 9920713 A1 | 4/1999 |
| WO | WO 0025380 A2 | 5/2000 |
| WO | WO 2007108014 A1 | 9/2007 |
| WO | WO 2008134871 A1 | 11/2008 |

*Primary Examiner* — Elvis O Price
(74) *Attorney, Agent, or Firm* — Coraline J. Haitjema; David P. Owen; Hoyng Monegier LLP

(57) ABSTRACT

Disclosed is a process for reacting carbon dioxide with hydrogen. In the process a catalyst having carbon dioxide adsorbed thereto is contacted with hydrogen at an elevated temperature. The catalyst can be regenerated by contacting depleted catalyst with a carbon dioxide source, for example a flue gas of a power plant. In a preferred embodiment carbon dioxide is reacted by in situ hydrolysis of water.

27 Claims, 1 Drawing Sheet

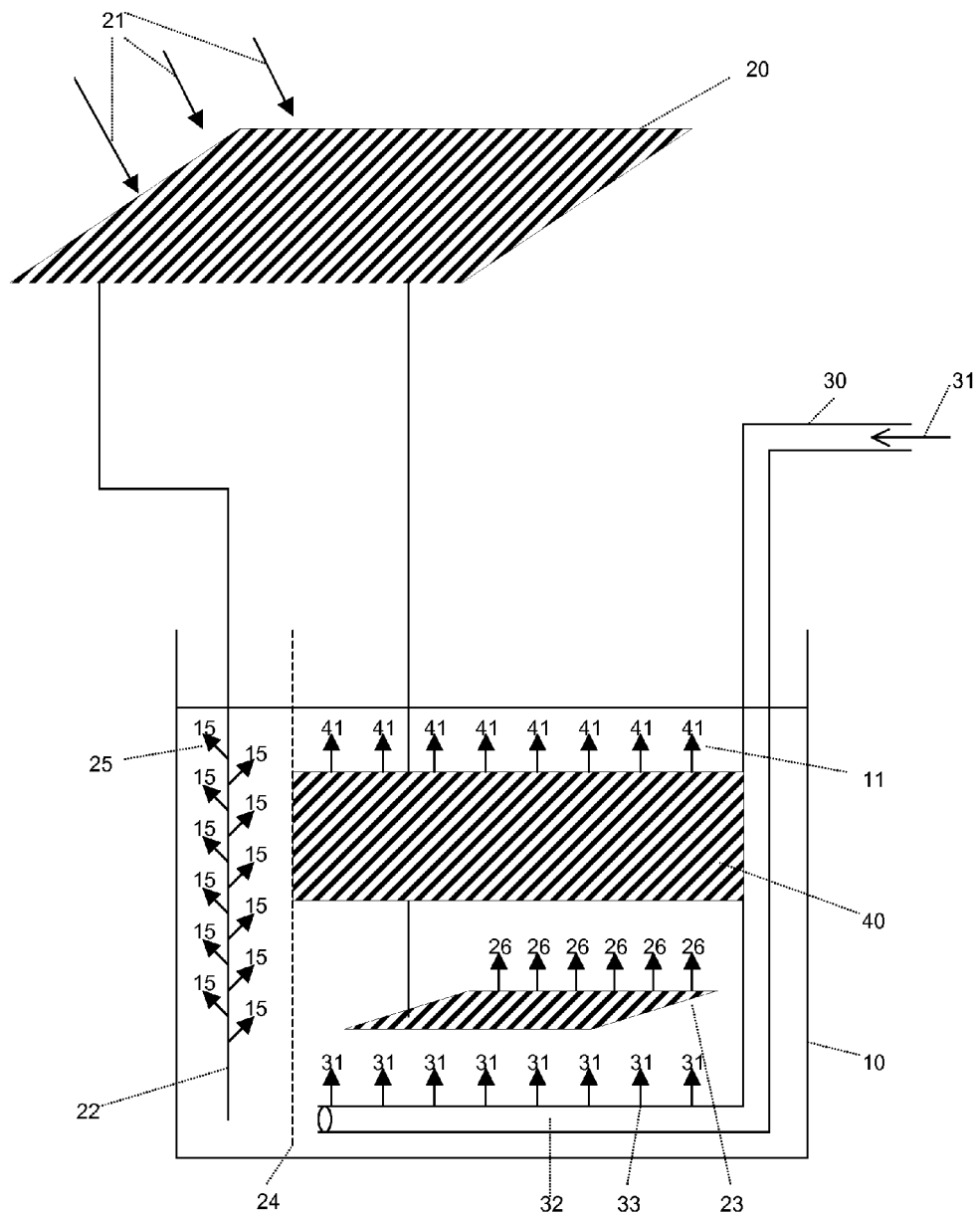

CATALYTIC PROCESS FOR REACTING CARBON DIOXIDE WITH HYDROGEN

CROSS-REFERENCE TO RELATED APPLICATIONS

This application is a continuation of PCT application number PCT/EP2010/069305 filed on 9 Dec. 2010, which claims priority from U.S. provisional application No. 61/285,227 filed on 10 Dec. 2009. Both applications are hereby incorporated by reference in their entireties.

BACKGROUND OF THE INVENTION

1. Field of the Invention

The invention relates generally to the conversion of carbon dioxide to hydrocarbons and more particularly to a catalytic process for the conversion of carbon dioxide to hydrocarbons.

2. Description of the Related Art

Processes have been proposed for the conversion of carbon dioxide to hydrocarbons. The prior art processes generally comprise a number of reaction steps.

DE 101 56 975 A1 discloses a four-step process. In the first step carbon dioxide is isolated from the earth's atmosphere. In the second step water is dissociated by electrolysis into hydrogen and oxygen. In the third step the carbon dioxide is reacted with the hydrogen to form carbon monoxide and water. In the fourth step a mixture of the carbon monoxide and additional hydrogen is converted to hydrocarbons and water.

DE 203 20 020 U1 discloses an integrated plant for the production of cement and hydrocarbons. Electric energy from a nuclear plant is used to dissociate water to form hydrogen. Carbon dioxide is reacted with hydrogen in a reverse water gas shift reactor to form carbon monoxide, which in turn is reacted in a Fischer-Tropsch reactor to form hydrocarbons.

A similar process (reverse water gas shift reaction of carbon dioxide and hydrogen, followed by a Fischer-Tropsch reaction) is disclosed in US 2005/0232833.

GB 2 418 430 A discloses a process in which carbon dioxide is enriched from the atmosphere, or a carbon dioxide rich flue gas is used. Carbon dioxide is reacted with hydrogen to hydrocarbons in a Fischer-Tropsch reaction. The document does not disclose how the carbon dioxide/hydrogen mixture is converted to the syngas feedstock required for the Fischer-Tropsch reaction.

GB 2 459 430 A discloses a process wherein carbon dioxide is extracted from the atmosphere by chemical and physical extraction. The carbon dioxide is subjected to catalytic hydrogenation in the presence of hydrogen obtained from electrolysis of water. In one embodiment carbon dioxide is reacted with hydrogen to methanol; in turn, methanol is converted to hydrocarbons in a Fischer-Tropsch process. In a second embodiment carbon dioxide is reacted to octane using two catalysts, a salt in addition to a nickel hydrogenation catalyst.

U.S. Pat. No. 4,339,547 discloses a process in which carbon dioxide is extracted from the atmosphere, for example using NaOH to form $Na_2CO_3$. Hydrogen is produced by electrolysis. Carbon dioxide is reacted with hydrogen over a copper catalyst to form methanol. Methanol is converted to hydrocarbons over a zeolite catalyst.

WO 00/25380 discloses a process for storing solar energy. In the process solar energy is converted to electric energy using photovoltaic cells. The electric energy is used in electrolysis to form hydrogen. The hydrogen is reacted with carbon dioxide to form methanol, which is used as a fuel in a methanol fuel cell to generate electric energy.

WO 99/20713 discloses an intricate process in which carbon dioxide generated in the combustion of a fossil fuel, such as methane, is reacted with hydrogen in a Sabatier reactor over a nickel catalyst.

WO 2007/108014 discloses a process in which carbon dioxide from an industrial combustion process is reacted with hydrogen from water electrolysis to form methanol. The methanol is converted to hydrocarbons in the Mobil methanol-to-gasoline (MTG) process.

Thus, there is a particular need for an improved catalytic process in which carbon dioxide sequestration is combined with its catalytic conversion. There is a particular need for such a process that uses a renewable energy resource for the production of hydrogen.

BRIEF SUMMARY OF THE INVENTION

The present invention addresses these problems by providing a process for reacting carbon dioxide with hydrogen, said process comprising the steps of:
(i) providing a catalytic material having carbon dioxide adsorbed thereto;
(ii) contacting the catalytic material of step (i) with hydrogen at a temperature in the range of from 25° C. to 1000° C., preferably from 200° C. to 500° C., whereby a reaction product is formed.

Another aspect of the invention comprises a method for regenerating the catalyst by contacting the catalyst after use in step (ii) with carbon dioxide.

DETAILED DESCRIPTION OF THE INVENTION

Various prior art processes are based on a reaction of carbon dioxide with hydrogen as a step towards the production of hydrocarbons. The processes vary in the source of the carbon dioxide reactant. In one class of processes carbon dioxide is captured from the atmosphere, for example by chemical or physical extraction. Other processes are integrated with an industrial process that inherently produces carbon dioxide, for example the combustion of fossil fuels in a power plant, or the decomposition of lime stone in the manufacture of cement. A third class of process comprises the sequestering of carbon dioxide from a flue gas. Yet other processes use air as an immediate source of carbon dioxide.

All of the prior art processes have significant disadvantages in the area of carbon dioxide generation. Processes that use air "as is" suffer from the very low concentration of carbon dioxide in ambient air, and the presence of oxygen. Processes that use a flue gas of a combustion process as the carbon dioxide source suffer from geographic and capacity constraints associated with integrated processes. That is, the hydrocarbon production plant must be located in close proximity of the carbon dioxide generating plant, and the capacity of the hydrocarbon production plant must closely match the carbon dioxide production rate of the plant with which it is integrated.

Processes that rely on carbon dioxide capture are more flexible in terms of the geographic location and the capacity of the hydrocarbon production plant. However, these processes introduce a new inefficiency in that the material used for capturing the carbon dioxide must be decomposed to free the captured carbon dioxide.

The present invention addresses the carbon dioxide sourcing issue by providing a process for reacting carbon dioxide with hydrogen, said process comprising the steps of:
(i) providing a catalytic material having carbon dioxide adsorbed thereto;

(ii) contacting the catalytic material of step (i) with hydrogen at a temperature in the range of from 25° C. to 1000° C., preferably from 200° C. to 500° C., whereby a reaction product is formed.

In other words, the catalyst used in step (ii) is a material that is suitable for capturing carbon dioxide. This eliminates the need for decomposing the carbon dioxide sequestering material in order to free up the carbon dioxide for reaction with hydrogen. Instead, the process of the invention provides carbon dioxide at the location where it is most needed, i.e., the surface of the catalyst. Hydrogen molecules, because of their small size, quickly and easily diffuse into the pores of the catalyst.

The process of the invention can be used for a variety of reactions between carbon dioxide and hydrogen. For example, the reaction product of step (ii) can comprise carbon monoxide, as in a reverse water gas shift reaction. In an alternate embodiment the reaction product comprises methanol. In yet another embodiment the reaction product comprises a mixture of hydrocarbons.

In processes in which the reaction product comprises a mixture of hydrocarbons the hydrocarbons preferably comprise a mixture of alkanes. The hydrocarbon mixture may further comprise a mixture of olefins.

The skilled person will appreciate that the composition of the reaction product will be largely determined by factors such as the reaction temperature, the hydrogen pressure, the presence or not of additional carbon dioxide, and the nature of the catalyst. In particular the nature of the catalyst plays an important role in determining the composition of the reaction product. For example, a reverse water gas shift catalyst favors the formation of carbon monoxide; a hydrogenation catalyst favors the formation of methanol; and a Sabatier catalyst or a Fischer-Tropsch catalyst favors the formation of hydrocarbons.

It can be advantageous to use a catalyst composition comprising two or three functions. One function that the catalyst composition must be able to provide is the adsorption of carbon dioxide. The catalyst composition may contain a second component for providing, for example, hydrogenation functionality or Fischer-Tropsch functionality. An example of a tri-component catalyst composition is one comprising a first component providing carbon dioxide adsorption functionality; a second component providing reverse water gas shift functionality; and a third component providing Fischer-Tropsch functionality.

The catalyst composition can comprise a metal oxide, for example an oxide of a divalent metal or an oxide of a trivalent metal.

The divalent metal can comprise an alkaline earth metal, in particular calcium and/or magnesium. The trivalent metal can, for example, be aluminum.

Particularly preferred are catalyst compositions comprising hydrotalcite or a hydrotalcite-like material. The term "hydrotalcite-like material" as used herein refers to materials having the general crystal structure of hydrotalcite and wherein part or all of the magnesium ions are replaced with ions of another divalent metal, and/or part or all of the aluminum ions are replaced with ions of another trivalent metal.

The catalyst composition can further comprise a transition metal. Preferred transition metals are those selected from the group consisting of Fe, Ni, Co, Ru, Re, Zn, Au, and mixtures thereof.

In a preferred embodiment the carbon dioxide conversion comprises in situ hydrolysis of water. Accordingly, a preferred embodiment of the invention is a process comprising the steps of:

(i) providing a water source and a catalytic material having carbon dioxide adsorbed thereto;
(ii) activating water from the water source using a form of solar energy, in the presence of the carbon source;
(iii) converting the carbon dioxide to organic compounds comprising carbon and hydrogen.

An important aspect of this embodiment of the process of the present invention is that the input of solar energy, which results in water in an activated form, takes place in the presence of the carbon source. This feature permits the carbon dioxide to react with water in the activated form.

This embodiment of the invention is not limited by specific forms of activated water. In one embodiment the water molecule has one or both of the O—H bonds in an excited state, making it possible for a hydrogen radical to be split off and react with the carbon source. The excited state can be achieved by irradiating water with solar photons, in particular in the UV range of the spectrum. The formation of activated water can be amplified by the use of a suitable semiconductor with a band gap corresponding to the energy of photons in the visible or near ultra-violet part of the spectrum. Titanium dioxide (band gap 3 eV) is an example of a suitable semiconductor material.

In another embodiment solar energy is used to form hydrogen radicals and/or hydrogen molecules. For example, solar energy can be used to generate electric energy in a photovoltaic process. The electric energy can be used for electrolysis of water molecules, whereby hydrogen in atomic form (hydrogen in statu nascendi) is formed. This form of hydrogen is far more reactive than molecular hydrogen. Atomic hydrogen reacts readily with the carbon source.

In yet another embodiment, a form of solar energy is used to dissociate water into hydrogen molecules. Although less reactive than atomic hydrogen, molecular hydrogen can react with the carbon source, in particular in the presence of a suitable catalyst.

The water source does not need to meet stringent requirements in terms of purity. In particular as compared to natural photosynthesis processes, the requirements imposed on the water quality by the process of the present invention are very low. Thus, the process can be carried out with water comprising at least one contaminant.

Specifically, the water source can comprise waste water. The waste water can be industrial waste water, municipal waste water, farm runoff, and the like.

In a particularly preferred embodiment, the water source comprises sea water. Minerals dissolved in sea water impart the water with a high conductivity, which is advantageous for electrolytic processes. The cations dissolved in sea water do not compete with protons for electron acceptance, so the formation of hydrogen is not impeded by their presence.

Solar energy can be used in the form in which it reaches earth, that is, in the form of electromagnetic radiation in the infrared, visible, and ultraviolet parts of the spectrum, i.e., photonic energy. It can be desirable to convert this photonic energy to some other form of energy, for example to permit the energy to be temporarily stored. Temporary storage makes it possible to run the process also when the sun is not shining, for example during night time. Relatively advanced technology exists for converting solar energy to photovoltaic energy, which can be stored in rechargeable batteries, for example Li-ion batteries.

The process of the invention itself can be used for storing solar energy in the form of an organic compound, such as an alcohol (for example ethanol or methanol), a hydrocarbon, or a carbohydrate. Preferably the organic compound is a liquid at room temperature, for cost effective storage and transportation. The organic compound can be used as a fuel in a fuel cell for generating electricity. Thus, solar electricity can be made available on a 24/7 basis (24 hours per day, 7 days per week).

Once converted to photovoltaic energy, solar energy can be readily converted to yet other forms of energy, such as microwave energy. It can be desirable to convert the photovoltaic energy back to photonic energy, in the form of a laser beam, for example. Laser permits energy to be submitted to the process in a highly concentrated form.

In an alternate embodiment solar energy is used to generate steam, for example in a Concentrated Solar Thermal (CST) process. The CST process uses lenses, mirrors and a tracking system to focus a large area of sunlight into a small area. The concentrated heat can be used for generating steam, which can be used to generate electricity in a conventional steam generator.

In a specific embodiment of CST the concentrated heat is used to raise the temperature of water to 800-1200° C. The overheated steam is contacted with oxygen-deficient ferrite materials containing transition metals such as zinc and/or nickel. The ferrite can be deposited on an inert support to increase the specific surface area, for example a ceramic honeycomb support. Under these conditions water dissociates into oxygen and hydrogen. Hydrogen can be used in step (iii) of the present process, either in situ, or in a separate reactor after removing oxygen from the hydrogen stream.

In yet another embodiment solar energy is converted in a Photon Enhanced Thermionic Emission (PETE) process. In a PETE process a metal-coated semiconductor material is irradiated with solar radiation. Different from the photovoltaic (PV) process, which only uses the visible part of the spectrum, the semiconductor of the PETE process is able to convert both the visible light and the IR parts of the solar spectrum to electric energy, making the PETE process much more efficient. The semiconductor material used in the PETE process must be able to withstand high temperatures. Suitable examples include gallium nitride and gallium arsenide.

In one embodiment step (ii) comprises a Fischer-Tropsch reaction. The Fischer-Tropsch reaction is essentially a reaction of carbon monoxide and hydrogen, to form hydrocarbons, in particular alkanes.

In this embodiment, the reaction mixture comprises carbon monoxide, which is reacted with hydrogen in statu nascendi, or with molecular hydrogen, or a mixture of the two. Accordingly, $CO_2$ is first reacted with hydrogen to form CO in the inverse water shift reaction, thereby providing the carbon source for the Fischer-Tropsch reaction.

It is desirable to conduct the Fischer-Tropsch reaction in the presence of a Fischer-Tropsch catalyst. Examples include catalysts comprising Ni, Fe, Co, Ru, Ce, or a combination thereof. It is advantageous to use a catalyst carrier that is capable of absorbing solar photonic energy, such as $TiO_2$. Step (ii) is preferably carried out while solar energy is supplied to the reaction mixture, for example in the form of photonic energy.

Traditional Fischer-Tropsch processes require high temperatures and high hydrogen pressures. The process of the present invention can be carried out under much milder conditions. This is believed to be due to the greater reactivity of the hydrogen, possibly amplified by photonic solar energy being supplied to the reaction mixture.

In an alternate embodiment, step (ii) comprises a Sabatier reaction, which uses carbon dioxide as the carbon source. Advantageously, carbon dioxide is present in a concentrated form in the process of the invention.

The Sabatier reaction is preferably carried out in the presence of a Sabatier catalyst. Particularly preferred are catalysts comprising Ru.

In a specifically preferred embodiment, the Sabatier catalyst comprises a hydrogenating metal, such as Ni or Ru, on a semiconductor support, such as $TiO_2$. The metal portion of the catalyst is only partially reduced. For example, a $Ru/TiO_2$ catalyst is reduced in an $Ar/H_2$ (1:1 ratio) stream, at a temperature in the range of 200° C. to 250° C. Full reduction of $RuO_2$ requires a reduction temperature of 500° C.

The $Ru/TiO_2$ catalyst permits the Sabatier reaction to be carried out under atmospheric pressure, at temperatures in the range of from 25 to 200° C. The catalyst is particularly effective when the reaction mixture is illuminated with solar photonic energy.

In yet another embodiment, the catalyst is an inorganic oxide or hydroxide. Catalysts of this type can be used with a wide variety of carbon sources, including coal and synthetic polymers.

Preferred within this class of catalysts are hydrotalcite; hydrotalcite-like materials; clays; alumina; layered hydroxy salts; mixed metal oxides; and the calcination products of any of these materials. The term "hydrotalcite-like" materials as used herein refers to mixed metal oxides having the general crystal structure of hydrotalcite, and wherein all or part of the $Al^{3+}$ is replaced with another trivalent cation, and/or all or part of the $Mg^{2+}$ is replaced with another divalent cation.

The type of organic compounds produced in step (iii) depends on the nature of the carbon source, and the type of reaction conducted. For example, if the carbon source is carbon dioxide, and the reaction is a Sabatier reaction, the primary (or sole) reaction product is methane. If the carbon source is carbon dioxide or carbon monoxide, and the reaction is a Fischer-Tropsch reaction, the reaction product is a mixture of hydrocarbons, primarily alkanes.

Methane produced in a Sabatier reaction can be readily converted to methanol, using well-known prior art processes. Methanol can be used as a fuel for a fuel cell.

The reaction product of step (ii) can be used as a feed in a subsequent conversion reaction. For example, a reaction product comprising methanol can be converted to a mixture of hydrocarbons in a methanol-to-gasoline (MTG) process. Similarly, a reaction product comprising carbon monoxide can be converted to a mixture of hydrocarbons in a Fischer-Tropsch (FT) process.

Desirably, at least step (ii) of the process is carried out in continuous mode.

During the reaction of step (ii), the catalyst becomes depleted with carbon dioxide. The catalyst can be regenerated by contacting the catalyst with carbon dioxide. In one embodiment the catalyst is contacted with air, and is allowed to adsorb carbon dioxide from the air. In a preferred embodiment the catalyst is contacted with a carbon dioxide-rich gas, for example flue gas.

The flue gas may be generated by a power plant, for example a power plant fired with a fossil fuel. The process of the present invention is particularly suitable for capturing and re-using carbon dioxide from a coal-fired power plant, as the flue gases of these power plants are particularly rich in carbon dioxide.

The hydrogen used in step (ii) can be from any source. Preferred is "carbon-free" hydrogen, for example hydrogen produced by water electrolysis using electric power from a renewable resource. Examples of renewable energy sources include solar power, wind power, and tidal power.

An important advantage of the process of the invention is that it can be carried out at a location where electricity from a renewable resource is abundantly available. One aspect of the process of the invention is its use for storing solar energy in the form of the reaction product of step (ii) or the reaction product of a subsequent reaction step. In a preferred embodiment the process of the invention stores solar energy in the form of hydrocarbons.

If hydrogen is produced by electrolysis, water is needed as a feedstock for the process. Importantly, water for the process can be of poor quality in terms of purity, so that water suitable for irrigation or for animal or human consumption does not need to be used in the process. For example, sea water or brackish water can be used.

It should be noted that step (ii) of the process produces water. For example, in the case of the production of carbon monoxide:

$$CO_2 + H_2 \rightarrow CO + H_2O \qquad (eq.\ 1)$$

For the production of methanol:

$$CO_2 + 3H_2 \rightarrow CH_3OH + H_2O \qquad (eq.\ 2)$$

And for the production of an alkane having n carbon atoms:

$$nCO_2 + (6n+2)H_2 \rightarrow C_nH_{2n+2} + 2nH_2O \qquad (eq.\ 3)$$

Water produced in step (ii) can be recycled to the water electrolysis step. However, in the embodiment in which the reaction product of step (ii) is a mixture of alkanes (equation 3), the water produced in the reaction is easily separated from the hydrocarbon reaction products. The water produced in the reaction can be readily purified to make it suitable for irrigation or even animal or human consumption. As the process can use sea water as a feedstock and has the ability to produce potable sweet water, this embodiment of the invention provides indirect water purification or desalination as a side benefit.

It will be readily understood that the process is particularly suitable for use in dry sunny areas close to a coastline, as both solar energy and sea water are abundantly available, and the water by-product can be put to good use.

Description of A Specific Embodiment

The invention will be further illustrated with reference to a specific embodiment shown schematically in FIG. 1.

Reactor 10 comprises a water source 11. Photovoltaic panel 20 receives solar photonic energy 21, which it converts to photovoltaic energy. The photovoltaic energy feeds anode 22 and cathode 23, both of which are immersed in water source 11. Anode 22 and cathode 23 are optionally separated by membrane 24.

Tube 30 receives a catalyst 31 having carbon dioxide adsorbed thereto from an external supply (not shown). Catalyst 31 is pumped to tube end 32, which is immersed in water source 11. Carbon source 31 leaves tube end 32 through holes 33.

Anode gas 25 is formed at anode 22. Anode gas 25 can be oxygen (from the electrolysis of OH⁻ ions in water source 11, or it can be some other gas, for example $Cl_2$, if water source 11 contains $Cl^-$ ions. Anode gas 25 is collected in a gas container (not shown).

Hydrogen gas 26 is formed at cathode 23. Both carbon source 31 and hydrogen gas 26 rise upward in water source 11, and become mixed with one another. The gas mixture passes through catalyst bed 40, where carbon dioxide present on catalyst 31 is reacted with hydrogen gas 26. Reaction product 41 is a liquid hydrocarbon, which floats to the surface of water source 11.

In an alternate embodiment the reaction product comprises gaseous hydrocarbons, which are collected above the surface of water source 11.

In yet another embodiment, the catalyst is slurried in water source 11, which is continuously agitated.

What is claimed is:

1. A process for reacting carbon dioxide with hydrogen, said process comprising the steps of:
   (i) providing a catalytic material having carbon dioxide adsorbed thereto;
   (ii) contacting the catalytic material of step (i) with hydrogen at a temperature in the range of from 25° C. to 1000° C., whereby a reaction product is formed; and
   (iii) the catalyst is regenerated by contacting the catalyst with air and allowing the catalyst to absorb carbon dioxide from the air.

2. The process of claim 1 wherein step (ii) is carried out at a temperature in the range of from 200° C. to 500° C.

3. The process of claim 1 wherein the reaction product comprises carbon monoxide.

4. The process of claim 1 wherein the reaction product comprises methanol.

5. The process of claim 1 wherein the reaction product comprises a mixture of hydrocarbons.

6. The process of claim 5 wherein the reaction product comprises a mixture of alkanes.

7. The process of claim 6 wherein the reaction product further comprises olefins.

8. The process of claim 1 wherein the catalytic material comprises an oxide of a divalent metal.

9. The process of claim 1 wherein the catalytic material comprises an oxide of a trivalent metal.

10. The process of claim 8 wherein the divalent metal comprises an alkaline earth metal.

11. The process of claim 9 wherein the trivalent metal comprises aluminum.

12. The process of claim 10 wherein the catalytic material comprises hydrotalcite or a hydrotalcite-like material.

13. The process of claim 10 wherein the catalyst catalytic material further comprises a transition metal.

14. The process of claim 13 wherein the transition metal is selected from the group consisting of Fe, Ni, Co, Ru, Re, Zn, Au, and mixtures thereof.

15. The process of claim 4 comprising the further step of converting methanol to a mixture of hydrocarbons in a methanol-to-gasoline (MTG) process.

16. The process of claim 3 comprising the further step of converting carbon monoxide to a mixture of hydrocarbons in a Fischer-Tropsch (FT) process.

17. The process of claim 1 wherein at least step (ii) is carried out in continuous mode.

18. The process of claim 1 wherein the used catalytic material is contacted with a flue gas.

19. The process of claim 18 wherein the flue gas is generated by a power plant.

20. The process of claim 19 wherein the power plant is fired with a fossil fuel.

21. The process of claim 1 wherein the hydrogen is produced by water hydrolysis.

22. The process of claim 21 wherein the water hydrolysis is carried out with electric power from a renewable resource.

23. The process of claim 22 wherein the renewable resource is selected from solar power; wind power; tidal power; and combinations thereof.

24. The process of claim 1 wherein, in step (i), the catalytic material comprises from 5 wt % to 40 wt % carbon dioxide.

25. The process of claim 11 wherein the catalyst comprises hydrotalcite or a hydrotalcite-like material.

26. The process of claim 11 wherein the catalyst further comprises a transition metal.

27. The process of claim 24 wherein, in step (i), the catalytic material comprises from 10 wt % to 30 wt %.

\* \* \* \* \*